(12) United States Patent
Hamasu et al.

(10) Patent No.: US 6,272,917 B1
(45) Date of Patent: Aug. 14, 2001

(54) DRAW-FALSE TWISTING MANAGEMENT SYSTEM

(75) Inventors: Bunji Hamasu; Katsushi Kikuchi; Isao Miyazaki, all of Matsuyama (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/471,280

(22) Filed: Dec. 23, 1999

(30) Foreign Application Priority Data

Jan. 29, 1999 (JP) ................................................. 11-021695

(51) Int. Cl.[7] .................................................. G01L 5/04
(52) U.S. Cl. .......................................... 73/160; 73/862.59
(58) Field of Search ............................ 73/160, 826, 828, 73/862.391, 862.392, 862.59; 57/264, 265

(56) References Cited

U.S. PATENT DOCUMENTS

| | | | |
|---|---|---|---|
| 4,376,364 | * | 3/1983 | Horino et al. ............................. 53/54 |
| 4,399,648 | * | 8/1983 | Kato ...................................... 57/265 |
| 4,445,322 | * | 5/1984 | Satterfield .............................. 57/264 |
| 4,692,615 | * | 9/1987 | Mensah et al. .......................... 73/160 |
| 5,502,961 | * | 4/1996 | Tone et al. .............................. 57/264 |

FOREIGN PATENT DOCUMENTS

| | | | |
|---|---|---|---|
| 52-152511 | 12/1977 | (JP) | .................. D02G/1/02 |
| 6-264318 | 9/1994 | (JP) | .................. D02G/1/04 |
| 7-138828 | 5/1995 | (JP) | .................. D02G/1/04 |

* cited by examiner

*Primary Examiner*—Max Noori
(74) *Attorney, Agent, or Firm*—Sughrue, Mion, Zinn, Macpeak & Seas, PLLC

(57) ABSTRACT

A draw-false twisting management system that measures untwisting tension with an untwisting tension sensor (13) and diagnoses trouble in a draw-false twisting machine, wherein the measured values are subjected to fast Fourier transform online by fast Fourier transform means (18), the untwisting tension signal is monitored in a frequency domain, a pattern is extracted for the integral value (area value) or peak value in a specific frequency band, and a comparative judgment against a preset reference pattern is made by trouble-judging means (19), which judges that trouble has occurred in the draw-false twisting when the value falls outside of the reference value range.

6 Claims, 3 Drawing Sheets

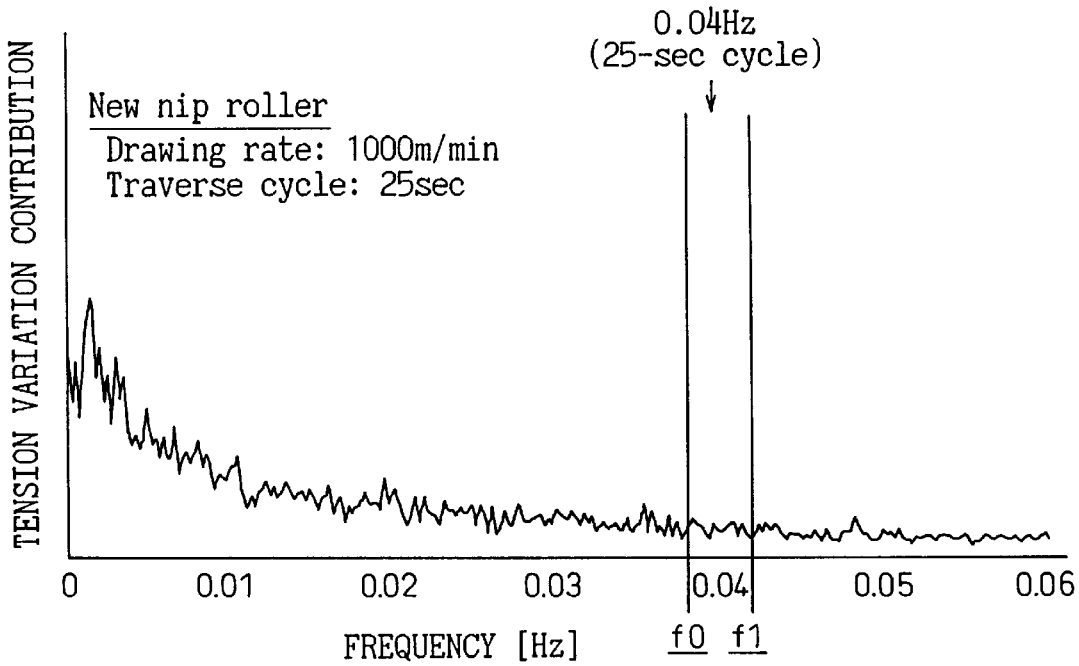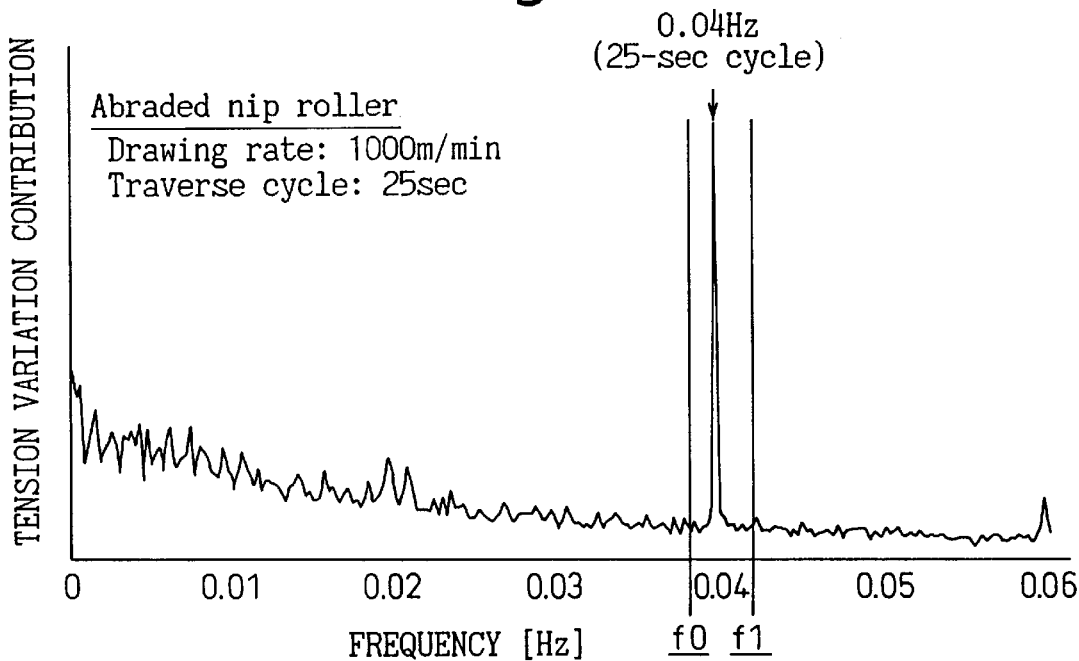

DRAW-FALSE TWISTING MANAGEMENT SYSTEM

BACKGROUND OF THE INVENTION

1. Field of the Invention

The present invention relates to a system that measures untwisting tension in a draw-false twisting machine and manages troubles occurring in the draw-false twisting machine itself and the quality of draw-false twisted textured yarn based on the data for the measured untwisting tension.

2. Description of the Related Art

Draw-false twisting machines for draw-false twisting of synthetic fibers made of thermoplastic resins such as polyester, nylon, etc. are widely used for production of false twisted textured yarn, by passing fed incompletely drawn yarn (hereunder referred to simply as "feed yarn") through a heater and drawing it while twisting with a false twisting unit. The twisting unit is included to provide twisting by keeping the yarn to run while in contact with a rotating friction surface at a fixed angle, and as twisting systems for the twisting unit there are known spindle twisting systems, belt twisting systems, friction disk twisting systems, etc. In all of these twisting systems, the feed yarn being twisted by the twisting unit is set by heating with heating means during the twisting step, after which it is untwisted to give it a false twisted shape and textured into false twisted yarn.

Incidentally, in the draw-false twisting step, defects in the feed yarn such as broken filaments and fluff appear as unusual untwisting tension. Consequently, it has become conventional to perform quality management in draw-false twisting machines, by time sequence monitoring of the untwisting tension, such as by the technique described in Japanese Unexamined Patent Publication No. 7-138828.

It has also become a recent practice to detect and measure untwisting tension with a tension sensor, such as by the technique described in Japanese Unexamined Patent Publication No. 6-264318, and to grade the quality on the packages of wound draw-false twisted yarn based on those results. Another method is to also add tension control means for adjustment of the yarn delivery force and the twisting force in the false twisting unit so that the untwisting tension falls within the target management range.

However, after much diligent research on untwisting tension, the present inventors have confirmed that the untwisting tension level often varies by about ±5 g depending on the properties of the feed yarn. If such large tension variation is arisen, it is highly possible that the feed yarn will experience some sort of trouble in processing under conditions that are different from normal, in a step other than the draw-false twisting step.

Despite this, uniformly maintaining the untwisting tension level within a management range by tension control means such as disclosed in Japanese Unexamined Patent Publication No. 6-264318 can result in failure to notice production trouble hysteresis even if the feed yarn that is fed to the draw-false twisting step is sometimes prepared under conditions with some sort of trouble. In the worst case, feed yarn that has experienced trouble may be subjected directly to the false twisting step and sent to the market as a textured yarn package.

In light of the circumstances alluded to above, the present inventors have diligently analyzed the factors involved in the variation in untwisting stress during the false twisting step, and as a result have found that this variation is closely related to the filament properties of the feed yarn, such as denier unevenness and orientation unevenness. It was also found that the following serious problems are inherent in conventional real-time untwisting tension monitor systems which simply monitor the actual values of untwisting tension online with the passage of time.

Specifically, it was found that if the untwisting tension is simply measured with the passage of time and the tension level value is managed within a given range or the cycle of the varying tension and the size of its amplitude is managed, to judge the stability of the process, this is completely ineffectual for judging what sort of trouble the feed yarn has undergone during processing, and the step in which it has occurred.

For this reason, even when variation occurs in the untwisting tension during the draw-false twisting step, it is very difficult to judge what trouble has occurred at which stage of preparation of the yarn fed to the draw-false twisting step, or what sort of trouble has occurred at what location in the draw-false twisting machine itself, and in fact absolutely no attempt has been made to discover these factors based on the untwisting tension.

Thus, a great deal of effort and time is required to investigate the cause of trouble with textured yarn or a problem of the draw-false twisting machine itself during the draw-false twisting step. In addition, the measures taken for the yarn preparation after discovering the cause are often delayed by a few weeks, and even when trouble occurs with the false twisting machine itself the trouble in the draw-false twisting machine is sometimes not realized and the problematic state therefore continues for future draw-false twisting.

Moreover, the values for the monitored untwisting tension variation include variation which is completely unrelated to the properties of the feed yarn, such as noise by machine vibration of the draw-false twisting machine, and its influence can result in misinterpretation of the data.

BRIEF SUMMARY OF THE INVENTION

In light of the current circumstances as described above, it is an object of the invention to provide a management system for a draw-false twisting machine which can immediately and accurately determine the location of trouble in different constituent elements of the draw-false twisting machine based on data for untwisting tension in the draw-false twisting machine and which can stabilize the draw-false twisting process.

The draw-false twisting management system of the invention is as follows.

1. A draw-false twisting management system which comprises managing troubles in a draw-false twisting machine itself and quality of a draw-false twisted yarn by measuring untwisting tension of the false-twisted yarn online, subjecting the measured untwisting tension signal to fast Fourier transform, and monitoring variation in the untwisting tension signal in a frequency domain.

2. A draw-false twisting management system according to 1. above, wherein the troubles in the draw-false twisting machine itself and the quality of the draw-false twisted yarn are managed by a comparative check between a pattern of the untwisting tension signal subjected to fast Fourier transform and a preset reference pattern.

3. A draw-false twisting management system according to 2. above, wherein the pattern of the untwisting tension signal subjected to fast Fourier transform is the integral value and/or peak value of the tension variation contribution in each frequency band determined by designating a specific frequency band at one or a plurality of locations, the threshold value being set for the integral value and/or peak value as a reference pattern, wherein it is judged that trouble has occurred when the determined integral value and/or peak value exceeds each threshold.

4. A draw-false twisting management system according to 1. above, which is provided with trouble judging means that monitors the specific frequency band of the untwisting tension signal subjected to fast Fourier transform at one or a plurality of locations, and judges the location and/or nature of trouble that has occurred in the draw-false twisting machine.

5. A draw-false twisting management system according to 1. above, which is provided with trouble judging means that monitors the specific frequency band of the untwisting tension signal subjected to fast Fourier transform at one or a plurality of locations, and judges the location and/or nature of trouble that has occurred during preparation of yarn fed to the draw-false twisting machine.

6. A draw-false twisting management system according to 1. above, which is provided with a tension detector for measurement of the untwisting tension of a yarn being false twisted online in the draw-false twisting machine, and discrete conversion means for discrete conversion of the untwisting tension signal detected by the tension detector.

BRIEF DESCRIPTION OF THE SEVERAL VIEWS OF THE DRAWING

FIG. 4 is a graph showing a typical mode of judging trouble in the draw-false twisting machine itself based on a pattern obtained by fast Fourier transform, for a case of normal operation.

FIG. 5 is a graph showing a typical faster Fourier transform pattern for judgment of trouble with the draw-false twisting machine itself, where a judgment of "trouble" has been made.

DETAILED DESCRIPTION OF THE INVENTION

The present invention will now be illustrated with reference to the attached drawings of embodiments of the invention.

Figure 1:
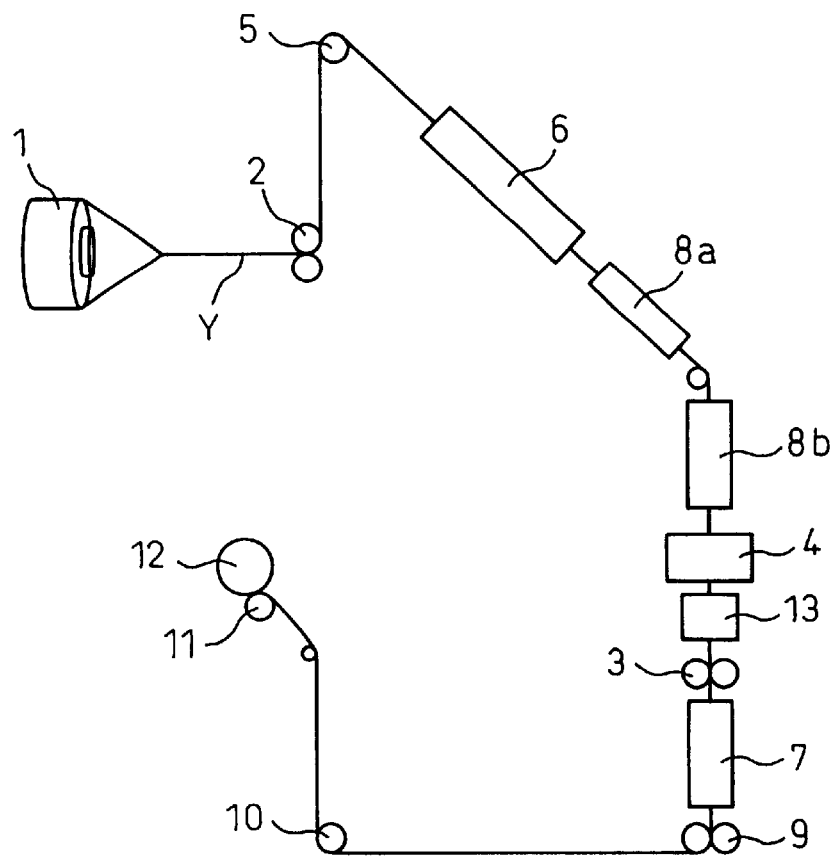
FIG. 1 is a schematic process diagram of a draw-false twisting machine used for the invention.
Figure 2:
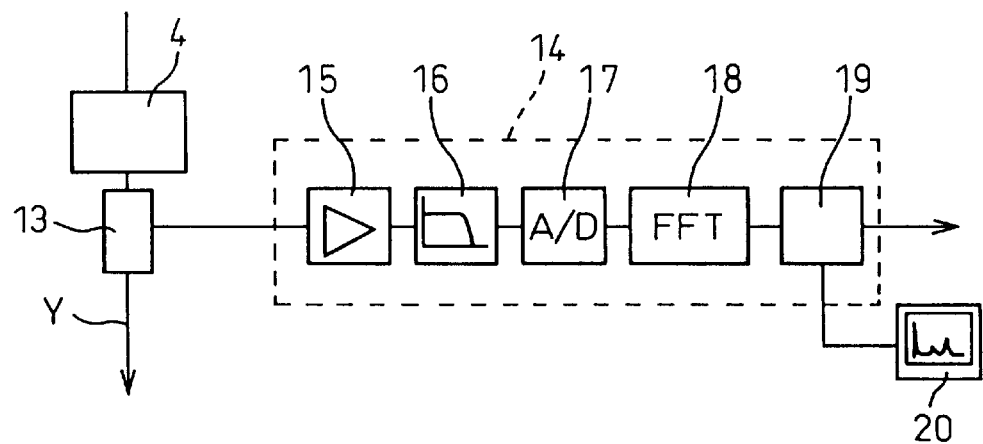
FIG. 2 is a block diagram showing a typical construction of a management apparatus according to the invention.
Figure 3:
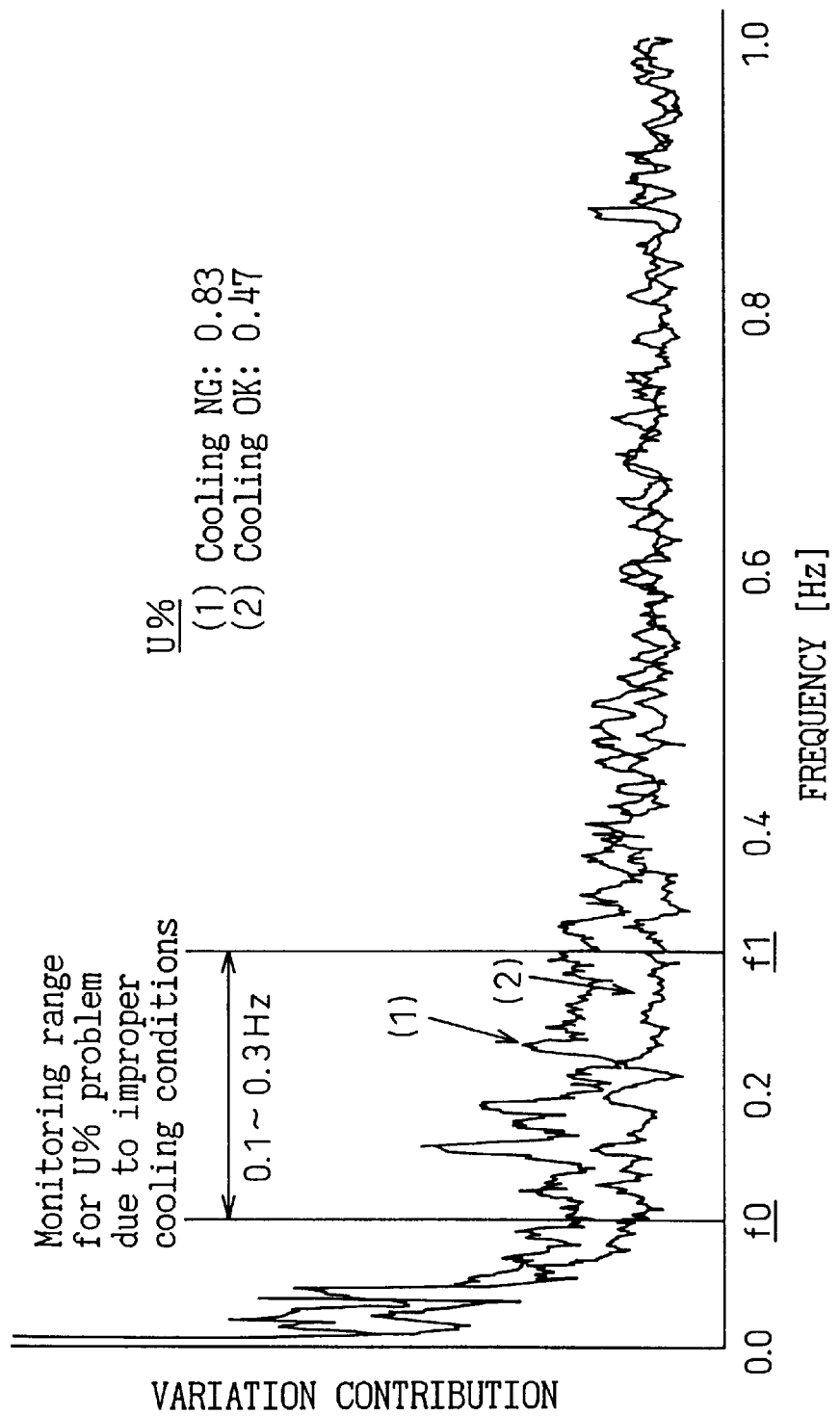
FIG. 3 is a graph showing a typical mode of judging trouble with feed yarn based on a pattern obtained by fast Fourier transform.

FIG. 1 is a general process diagram schematically illustrating a draw-false twisting process employing a draw-false twisting management system of the invention and an apparatus therefor. FIG. 2 is a block diagram showing typical trouble judging means (a management system) for a draw-false twisting machine according to the invention. FIGS. 3 to 5 are frequency graphs showing the results of measurement of the untwisting tension in draw-false twisting machines and fast Fourier transform of the measured tension.

In FIG. 1, 1 is a feed yarn package, and the yarn Y is drawn out from the feed yarn package 1 by a feed roller 2 and fed to a draw-false twisting machine. The feed yarn Y is then twisted by a false twisting unit 4 situated upstream from a conveying roller 3, and is retroactively twisted up to a twist stopping guide 5. The retroactive twisting up to the twist stopping guide 5 is thermally set by a heating apparatus 6, by which the twisted shape is set. Cooling apparatuses 8a and 8b perform cooling of the heated yarn Y. Here, a second heating apparatus 7 is used when necessary to modify the properties of the textured yarn. Finally, the yarn Y whose twisting has been set is conveyed to a winder 11 by conveying rollers 9 and 10, and wound up as a draw-false twisted yarn package.

In the draw-false twisting management system and apparatus according to the invention for a draw-false twisting process having this construction, it is a major feature that the untwisting tension of the draw-false twisting yarn is measured online, various data are drawn from the measured untwisting tension, and their content is analyzed to determine problems (troubles).

In other words, during the draw-false twisting, the untwisting tension detected by the tension detector 13 includes detection of untwisting tension as a complex of a number of overlapping factors including the tension due to drawing, the heat shrinkage due to heating, the frictional force of the guide, etc., and variable tension arisen by trouble in the draw-false twisting machine itself, all of which have a strong correlation with the properties of the feed yarn. Thus, if analysis of the untwisting tension which is a complex of these various overlapping factors can separately determine the different factors, it will be possible to distinguish which of the separated factors is responsible for the trouble, based on the analyzed data. The major feature of the present invention is the realization of this by the means of fast Fourier transform.

The present invention, therefore, first requires accurate online measurement of the untwisting tension among which the various overlapping factors are included. In order to achieve this object, a tension detector (sensor) indicated by numeral 13 in FIG. 1 is provided downstream from the false twisting unit 4, to continuously detect the untwisting tension. The tension detector 13 is commonly one which, for example, detects untwisting tension with a ceramic tension pickup guide for detection of the untwisting tension of yarn being worked by counterforce, and converts the detected counterforce to an electrical signal. The detection circuit used may generally be that of a known tension detector with a hall device that generates an electrical signal such as voltage, etc. in response to applied force, or a contact or non-contact potentiometer that converts a potential generated by applied force to an electrical signal such as voltage, etc. In this case, it will be an obvious point to avoid an adverse effect on the properties or handleability of the yarn being worked by considering the material, shape and mounted position of the tension pickup guide.

As explained above, the system monitors and manages troubles with the draw-false twisting machine itself and troubles with the feed yarn by subjecting the detected untwisting tension to fast Fourier transform and processing the data in various ways; this will now be illustrated with reference to FIG. 2.

In FIG. 2, an untwisting tension signal (analog signal) detected online in a time sequence manner by the tension detector 13 situated downstream from the false-twisting unit 4 is converted to an electrical signal and incorporated into a management device 14, and after amplifying the signal by an amplifier 15, it is preprocessed by removal of the unnecessary high frequency components and low frequency components by a band pass filter 16.

This preprocessed untwisting tension signal (analog signal) is then converted to a digital signal by discrete conversion and quantization of the analog signal at a prescribed sampling interval by an A/D (analog/digital) converter. The fast Fourier transform means 18 converts the time-domain data to frequency domain data, to obtain an untwisting tension signal pattern in the frequency domain. The untwisting tension signal pattern obtained in this manner is compared against a reference pattern by comparison means 19, and the result is outputted to a display 20 and inputted to problem-judging means such as a host computer (not shown) for judgment of the existence of trouble. The host computer (not shown) saves and stores the analyzed data to be utilized as basic data for further data analysis.

According to the invention, it is essential to analyze the untwisting tension as a complex of a number of overlapping factors, as mentioned above, in order to reseparate and extract each of the overlapping factors to accurately determine the problem. It is therefore necessary to eliminate the unwanted noise through preprocessing, and this is accomplished by converting the untwisting tension signal detected by the tension detector 13 to an electrical signal, incorporating it into the management device 14 and amplifying it with the amplifier 15, and then eliminating the unwanted noise components with the band pass filter 16. At this time, an anti-aliasing filter may be actively introduced to eliminate aliasing produced by the fast Fourier transform processing.

Next, the untwisting tension signal that has been preprocessed in the manner described above is subjected to discrete conversion (sampling) by the A/D converter 17 and then quantized, and the discrete conversion is carried out at the sampling frequency set by the fast Fourier transform means 18. The sampling frequency, of course, must be set to a frequency of at least twice the measured frequency range, according to a publicly known sampling constant, and must be a frequency that is extractable by separation of the various overlapping data for the untwisting tension.

Thus, the fast Fourier transform is performed by the fast Fourier transform means 18 based on data consisting of the discrete-converted and quantized untwisting tension signal, and the untwisting tension signal is converted from a time domain to a frequency domain. The untwisting tension signal thus converted to a frequency domain is used finally as analysis data to diagnose the location of trouble occurring at each element of the draw-false twisting machine, or the cause and location of trouble occurring during preparation of the yarn Y fed from the feed yarn package 1.

In the untwisting tension data analysis process described above, the first step is to search for a tension variation-contributing pattern for each frequency of the untwisting tension signal subjected to fast Fourier transform. Such a pattern may be, for example, an integral value (area value) determined by integrating the tension variation contribution across the specified frequency band, or the peak value of the tension variation contribution within the specified frequency band.

However, when one trouble event has occurred and two or more closely related factors are involved, it is sometimes impossible to determine the trouble simply by monitoring the specified frequency band at one location. In such cases it is necessary to simultaneously monitor a plurality of specified frequency bands. Here, small variations in the tension variation contribution at each frequency may be ignored, and only the waveform pattern for large variation may be extracted and the large variation pattern compared as a representative pattern. That is, a number of different-sized form patterns for the tension variation contribution at each frequency may be prepared and these form patterns compared. This is accomplished by subjecting the patterns to computation according to a program already inputted in the host computer, and comparing the results with an already inputted reference pattern.

However, when threshold values such as the integral value (area value) and peak value are used as comparative patterns, only one single value is compared without using the host computer, thus allowing easy and rapid data processing as well as accurate judgment in most cases of expected "trouble", although not universally. In such cases, the draw-false twisting system is judged as having "trouble" when the preset integral value (area value) and peak value thresholds are compared with the calculated integral value (area value) and peak value and the calculated integral value (area value) and peak value exceed the respective threshold values. According to the invention, therefore, it is possible to advantageously use the threshold value of the integral value (area value) or peak value as patterns of the tension variation contribution for each frequency of the untwisting tension signal. Furthermore, the draw-false twisting management system and management apparatus therefor allow for the first time monitoring of troubles in the draw-false twisting machine itself and trouble with the feed yarn, which has not been possible according to the prior art, so that the draw-false twisting system may be managed properly.

The monitored "specific frequency band" mentioned above is completely determined by the set conditions, such as the working speed of the draw-false twisting machine, the traversing speed or the yarn guide setting position. Thus, by presetting the desired specific frequency band corresponding to the factor to be analyzed, it is possible to judge trouble with regard to the factor being monitored. Needless to mention, the pattern of the threshold value of the integral value or peak value can also be set as desired.

When making a comparative judgment of complex patterns, the data used for these analyses are inputted into the host computer as trouble-judging means for the location of trouble for each element composing the draw-false twisting machine, and data analysis processing is carried out by the computer. In other words, a reference pattern is pre-inputted into the computer for each pattern data of an integral value or peak value that is to be judged as trouble-indicating data composed of a plurality of specific frequency bands, and trouble may be judged by checking against these reference patterns. However, for simple judgment of whether or not a specific threshold value (pattern) had been exceeded, it is possible to judge the trouble by constructing an electrically simple comparison circuit as trouble-judging means, without performing a complex computation for pattern extraction and comparison with the host computer. The specific frequency band data used for the analysis can be employed as trouble analysis data for the draw-false twisting machine itself and/or the feed yarn, so long as it occurs with different kinds of periodic variation.

The management system according to the invention as described above allows swift detection of the cause and location of trouble in a draw-false twisting machine wherever it occurs, by monitoring the aforementioned specific frequency band. That is, as a result of diligent research by the present inventors in regard to untwisting tension, it has become possible to diagnose trouble in the draw-false twisting step by monitoring a specific frequency band among data included in untwisting tension variation, even through the untwisting tension level varies by about ±5 g depending on the properties of the feed yarn.

A concrete example of applying the management system of the invention will now be explained in detail with reference to FIGS. 3 to 5. In FIG. 3, the curve (1) indicates a trouble situation in the preparation step for yarn to be supplied in the draw-false twisting step, and the curve (2) indicates production under normal processing conditions.

First, FIG. 3 shows a case of fast Fourier transform processing focused on a U % problem (problem of denier unevenness in the lengthwise direction of the yarn) due to a cooling defect in yarn Y fed to the draw-false twisting step. Here, the working speed of the draw-false twisting machine was 1000 m/min, the draw ratio was 1.795, the feed yarn Y was partially oriented yarn (POY) spun at 3000 m/min, the U % for the cooling defect (1) was 0.83, and the U % for proper cooling (2) was 0.47. The frequency band range of 0.1 Hz (f0)–0.3 Hz (f1) as shown is set as the specific frequency band for monitoring of cooling defects in the spinning step for the yarn Y supplied to the draw-false twisting step. Threshold values are preset for the integral value (area value) or peak value of this set frequency band of f0–f1. Here, the threshold value for the integral value (area value) has been set to 0.6. Thus, the calculated integral value (0.83) is compared with the set threshold value (0.6), and when the calculated integral value exceeds the threshold value it may be judged that a problem has occurred with the U% during the spinning step of the yarn supplied to the draw-false twisting step.

In other words, if the results shown in FIG. 3(1) are obtained (a U % integral value of 0.83), the cooling conditions in the spinning step of the feed yarn are judged as unacceptable (NG), and this result is inputted to the host computer (not shown) and outputted by a display 20. However, if the result is as shown in FIG. 3(2) (a U % integral value of 0.47), which is smaller than the set threshold value (0.6), the feed yarn Y can be considered as having been spun under proper cooling conditions (OK).

Incidentally, in addition to the U % in the specific frequency band used to judge trouble with the feed yarn Y, there may also be mentioned other factors for judging trouble, such as the throat pressure fluctuation frequency and the winding width cycle of the feed yarn package 1. The "specific frequency band" for each of these factors is determined by examining the hysteresis of yarn trouble that has occurred in the past, and it is established for each factor for constant online comparison when a problem pattern occurs. Here, a reference pattern (for example, the integral value or peak value threshold) is determined in advance to judge abnormal values, and the result is pre-inputted into a host computer or the like. The trouble conditions or the location that has experienced trouble (the trouble step) is discovered by comparing each pattern from the analyzed data. Such contrast with the hysteresis of the feed yarn Y results in feedback data for judgment of abnormal processing in a yarn preparation step prior to the draw-false twisting step, such as the spinning step, which is effective data for rectifying the processing conditions. Once a problem has occurred it is possible to immediately judge what sort of trouble it is, and rapidly specify the trouble that has occurred, and carry out the preset solution method. This eliminates the need to first analyze and deal with problems after they have occurred, as according to the prior art.

A management system for rapidly dealing with trouble that has been analyzed as "trouble occurring in the draw-false twisting machine itself" will now be explained with reference to FIGS. 4 and 5.

FIGS. 4 and 5 are graphs showing examples of fast Fourier transform processing for abrasion of a nip roller mounted on a yarn feed roller 2 of a draw-false twisting machine. FIG. 4 shows a case using a new product with no abrasion of the nip roller, and FIG. 5 shows a case using an abraded nip roller (40–60 Mm abrasion). Here, the draw-false twisting machine working speed was 1000 m/min, and to reduce the abrasion of the nip roller, the traverse cycle of the yarn for variation of the holding position of the yarn by the nip roller was 25 seconds. The specific frequency band $f_0$–$f_1$ for monitoring of the nip roller abrasion was set in a range of 0.038–0.042 Hz centered around 0.04 Hz, because of the traverse cycle of 25 seconds.

Also, the integral value (area value) from integration of the contribution of tension variation for each frequency in the specific frequency band of $f_0$f1, or the peak value of the tension variation contribution in that band, is calculated as a pattern for comparison with a reference pattern. The calculated pattern is then compared with a preset reference pattern (for example, the threshold value of the integrated value or peak value). Thus, if a peak value exceeding the threshold value is calculated as in FIG. 5, this results in a judgment that the abrasion of the nip roller of the draw-false twisting machine has increased, and this result is inputted to a host computer (not shown) and displayed by a display 20. By monitoring the specific frequency band determined by the conditions set for the mechanical elements of the draw-false twisting machine (for example, the winder traverse, the distance between yarn guides, etc.), and making continuous online comparative judgment, it is possible to obtain feedback data for process management of the draw-false twisting machine and implement a swift solution in the case of trouble.

Incidentally, because of the nature of the present invention utilizing fast Fourier transform, which is not suitable for event tension (instantaneous tension increase) or detection of yarn breakage, it is preferably used in conjunction with a conventional untwisting tension system. It will be readily appreciated that when used in conjunction with a conventional system, since the system of the invention measures the untwisting tension online in a substantially continuous manner, it can be very easily used with the conventional system and of course the conventional system can be satisfactorily used with the techniques described above under the Description of the Related Art.

According to the present invention, the untwisting tension signal from a draw-false twisting machine is subjected to fast Fourier transform processing, thus allowing accurate assessment of the location and nature of trouble occurring in the draw-false twisting machine itself and/or the feed yarn by online monitoring of the untwisting tension in a frequency domain. It is therefore possible to greatly reduce cost and labor expended to search for causes of trouble. Problems can therefore be discovered at the preparation stage of yarn fed for draw-false twisting, thus allowing the yarn preparation step to be improved. The equipment can also be improved before frequent equipment trouble occurs in the draw-false twisting machine. Another notable effect provided is stabilization of the draw-false twisting step and/or easier and faster management of processed yarn quality control.

The present invention can not only be applied for management of trouble in the process or with the feed yarn by monitoring of expected trouble, but can also advantageously deal with accidentally detected trouble that occurs unexpectedly. That is, when an unknown abnormal pattern never seen in the prior art appears in the pattern obtained from an untwisting tension signal transformed to a frequency domain by fast Fourier transform processing, the location and cause of the abnormal pattern can be investigated and identified as an unknown trouble phenomenon, allowing fast and accurate measurement to be taken when the same phenomenon occurs later.

This is because of the nature of the management system of the invention which monitors untwisting tension in the frequency domain, such that when an unknown trouble occurs, it is possible to immediately know the "specific frequency band" in which it has occurred. Thus, based on the data for the "specific frequency band", it is possible to easily investigate where the unknown trouble has occurred by finding the periodic cycle and phenomenon having that "specific frequency band". Moreover, since these data are constantly recorded and stored in a host computer, the stored data can be read out and reproduced to allow monitoring and management of draw-false twisting with high precision.

In addition, since the management system of the invention handles data converted into the frequency domain by fast Fourier transform, it is easy to eliminate normal permissible variation attributable to variation in the characteristics of the feed yarn which is already known, as well as mechanical vibration, electrical power noise, etc., thus providing an effect of drastically improved reliability of processing data.

What is claimed is:

1. A draw-false twisting management system which comprises measuring an untwisting tension of a draw false-twisted yarn online, converting the detected untwisting tension to an untwisting tension signal, subjecting the untwisting tension signal to fast Fourier transform, analyzing each variation contribution of frequency components of the fast-Fourier-transformed untwisting tension signal in a frequency domain, and judging problems in a draw-false twisting machine itself and quality of the draw-false twisted yarn from the analyzed variation contribution.

2. The draw-false twisting management system according to claim 1, wherein said problem is are judged from a comparative check between a pattern of said variation contribution and a preset reference pattern.

3. The draw-false twisting management system according to claim 2, wherein said pattern of the variation contribution is at least one of an integral value and a peak value of the variation contribution in each frequency band determined by designating a specific frequency band at more than one location, a threshold value(s) being respectively set for at least one of said integral value and said peak value as a reference pattern, wherein it is judged that a problem has occurred when at least one of the determined integral value and the determined peak value exceeds the corresponding threshold value.

4. The draw-false twisting management system according to claim 1, which is provided with problem judging means that monitors the specific frequency band of the fast-Fourier-transformed untwisting tension signal at more than one location, and judges at least one of the location and nature of a problem that has occurred in the draw-false twisting machine.

5. The draw-false twisting management system according to claim 1, which is provided with problem judging means that monitors the specific frequency band of the fast-Fourier-transformed untwisting tension signal at more than one location, and judges at least one of the location and nature of a problem that has occurred during preparation of yarn fed to the draw-false twisting machine.

6. The draw-false twisting management system according to claim 1, winch is provided with a tension detector for measurement of the untwisting tension of a yarn being false twisted online in the draw-false twisting machine, and discrete conversion means for discrete conversion of the untwisting tension signal detected by tension detector.

* * * * *